(12) United States Patent
Kim et al.

(10) Patent No.: US 6,502,695 B1
(45) Date of Patent: Jan. 7, 2003

(54) INDIVIDUALLY PACKAGED ABSORBENT ARTICLE AND A METHOD FOR MAKING THE SAME

(75) Inventors: Doo-Hong Kim, Seoul (KR); Hyung-Bum Kim, Seoul (KR); Eo-Yeon Hwang, Seoul (KR); Eun-Jung Kang, Seoul (KR)

(73) Assignee: Yuhan-Kimberly Ltd., Seoul (KR)

( * ) Notice: Subject to any disclaimer, the term of this patent is extended or adjusted under 35 U.S.C. 154(b) by 0 days.

(21) Appl. No.: 09/700,670

(22) PCT Filed: May 24, 1999

(86) PCT No.: PCT/KR99/00259
§ 371 (c)(1),
(2), (4) Date: Nov. 17, 2000

(87) PCT Pub. No.: WO99/60965
PCT Pub. Date: Dec. 2, 1999

(30) Foreign Application Priority Data

May 23, 1999 (KR) .............................................. 98/18701

(51) Int. Cl.[7] .......................... A61L 15/00; A61F 13/15
(52) U.S. Cl. ...................... 206/440; 604/387; 604/385.1
(58) Field of Search ............................... 206/438, 440, 206/441; 604/358, 387, 385.1, 393

(56) References Cited

U.S. PATENT DOCUMENTS

| 4,285,343 A | | 8/1981 | McNair | |
|---|---|---|---|---|
| 4,556,146 A | | 12/1985 | Swanson et al. | |
| 4,589,876 A | | 5/1986 | Van Tilburg | |
| 5,413,568 A | * | 5/1995 | Roach et al. | 604/358 |
| 5,472,437 A | * | 12/1995 | Akiyama et al. | 604/385.1 |
| 5,478,336 A | * | 12/1995 | Pigneul | 604/385.1 |
| 5,484,636 A | * | 1/1996 | Berg, Jr. et al. | 428/40 |
| 5,868,727 A | * | 2/1999 | Barr et al. | 604/387 |
| 6,036,679 A | * | 3/2000 | Balzar et al. | 604/387 |

FOREIGN PATENT DOCUMENTS

| EP | 527171 B1 | 10/1996 |
|---|---|---|
| EP | 0749742 A2 | 12/1996 |
| EP | 637234 B1 | 4/1997 |
| GB | 2 273 279 A * | 6/1994 |
| JP | 09220255 A | 8/1997 |
| JP | 09266928 A | 10/1997 |
| JP | 10338627 A | 12/1998 |
| SE | 5045514 | 12/1995 |

* cited by examiner

Primary Examiner—Mickey Yu
Assistant Examiner—Jila M Mohandesi

(57) ABSTRACT

An individually packaged absorbent article and a method for making the same is disclosed. The individual package comprises an absorbent pad having side tabs and a wrapper having a central release strip which may be parallel or perpendicular to the longitudinal axis of the wrapper. On either side of the central release strip are tab release members, the tab release members and the central release strip being permanently attached to the wrapper. The wrapper and the absorbent pad are folded as a unit about at least two lateral spaced-apart fold lines.

14 Claims, 6 Drawing Sheets

INDIVIDUALLY PACKAGED ABSORBENT ARTICLE AND A METHOD FOR MAKING THE SAME

CROSS-REFERENCE TO RELATED APPLICATIONS

This application is a 35 U.S.C. §371 national stage application based on PCT Application Serial No. PCT/KR99/00259, filed May 24, 1999 with a priority date of May 23, 1998.

BACKGROUND OF THE INVENTION

This invention generally relates to an individually packaged absorbent article such as a sanitary napkin. More specifically, this invention is directed to the package and a method of packaging an absorbent article which effectively protect the absorbent article prior to use and facilitate the removal of the absorbent article from the package.

It is well known in the art to individually package an absorbent article such as a sanitary napkin so that it is protected from soiling and contamination before use. Also, an individually packaged absorbent article allows the user to carry one or two absorbent articles in a purse or pocket for later use without damage or soiling. U.S. Pat. No. 4,556,146 to Swanson et al. discloses an individually packaged disposable absorbent article. According to the Swanson patent, a wrapper overlays one major surface of the article. The wrapper and the absorbent article are folded as a unit and the side edges of the wrapper are frangibly sealed to provide an individually packaged absorbent article.

Also, it is well known in the art that absorbent articles such as disposable sanitary napkins have side tabs. Side tabs are used to prevent menstrual liquid from contacting the wearer's underwear, and to hold the absorbent article against the wearer's underwear and maintain the absorbent article in a wearing position. For example, sanitary napkins having side tabs are disclosed in U.S. Pat. No. 4,285,343 to McNair and U.S. Pat. No. 4,589,876 to Van Tilburg. European Patent No. 0 527 171 to Davis et al. and European Patent No. 0 637 234 to 3M Company disclose sanitary napkins with side tabs folded over the topsheet, which are intended to protect the top sheet from damage or contamination until the tabs are unfolded for use. Furthermore, the European '171 and '234 patents teach that the side tabs are maintained in a folded position by a release strip attached to adhesive patches on the back surface of the side tabs.

However, the European '171 and '234 patents do not teach or suggest a technology for individually packaging sanitary napkins with side tabs. Moreover, in order to install the sanitary napkins on underwear, the user has to remove the release strip from the side tabs. Therefore, a technology is needed for individually packaging an absorbent article having side tabs which effectively protects the packaged absorbent article from damage and contamination and facilitates the removal of the absorbent article from the package for use.

SUMMARY OF THE INVENTION

In one aspect, the present invention provides an individually packaged absorbent article comprising an absorbent pad having two longitudinal and two lateral margins, a liquid pervious topsheet, a liquid impervious backsheet having adhesive elements formed thereon, an absorbent core interposed between the topsheet and the backsheet, and two tabs each extending outwardly from each longitudinal margin of said absorbent pad and having adhesive elements on the surface coextensive of said backsheet, and a wrapper having a central release strip which is attached to the wrapper and a pair of tab release members which are attached to the wrapper on each side of the central release strip. In the packaged absorbent article, the adhesive elements on the backsheet and the tabs are attached to the central release strip and the tab release members, respectively, and the absorbent pad is folded about at least two spaced-apart fold lines, and the wrapper is folded about at least two spaced-apart fold lines.

The invention also provides a method for individually packaging an absorbent article comprising an absorbent pad having a liquid pervious topsheet, a liquid impervious backsheet having adhesive elements formed thereon, an absorbent core interposed between the topsheet and the backsheet, and two tabs each extending outwardly from longitudinal margins of said absorbent pad and having adhesive elements thereon. The method comprises the steps of providing a wrapper in a generally flat position, affixing a central release strip to the wrapper and affixing a pair of tab release members to the wrapper on each side of the central release strip, releasably attaching the adhesive element on the backsheet to the central release strip and releasably attaching the adhesive elements on the tabs to the tab release members, folding the absorbent pad about at least two space-apart fold lines, and folding the wrapper about at least two spaced-apart fold lines to enclose the folded absorbent pad.

BRIEF DESCRIPTION OF THE DRAWINGS

Corresponding reference characters indicate corresponding parts throughout the several views of the drawings.

DETAILED DESCRIPTION OF EMBODIMENTS

Figure 1:
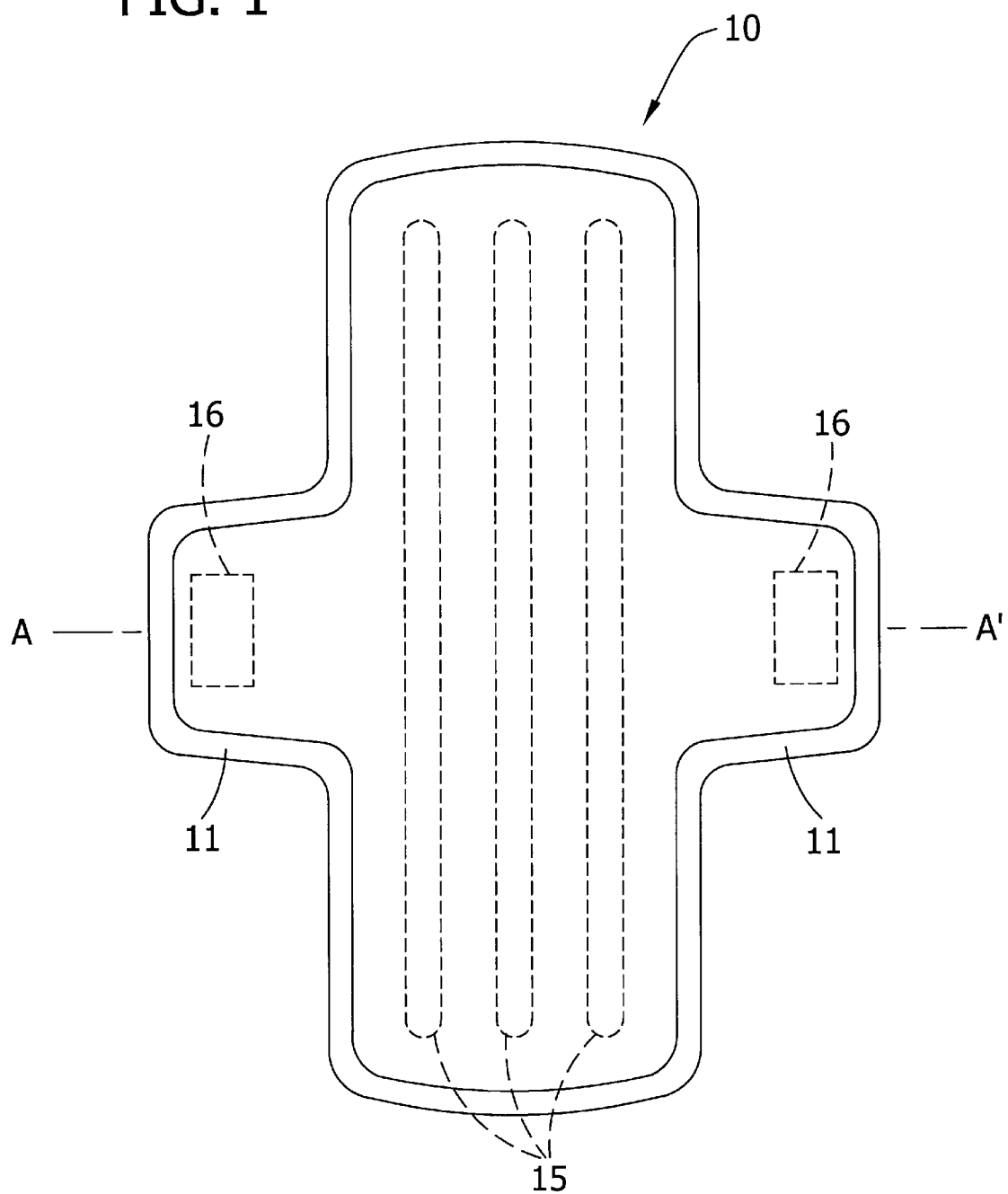
FIG. 1 is a plan view of an absorbent pad with side tabs.
Figure 2:
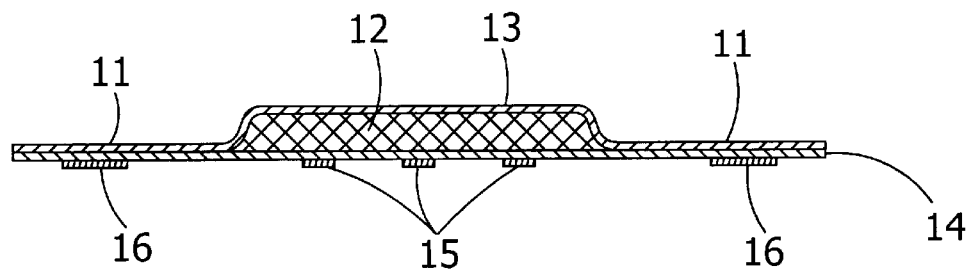
FIG. 2 is a sectional view of the absorbent pad of FIG. 1 taken along line A–A' of FIG. 1.

FIGS. 1 and 2 are plan and sectional views, respectively, of an absorbent pad 10 having side tabs 11. The absorbent pad 10 has two longitudinal and two lateral margins, a liquid pervious topsheet or liner 13, a liquid impervious backsheet or covering 14 having adhesive elements 15 formed thereon, and an absorbent core 12 interposed between the topsheet 13 and the backsheet 14. A tab 11 extends laterally outward from each longitudinal margin of the absorbent pad 10. Each tab 11 has an adhesive element 16 on a back surface thereof. The side tabs 11 are formed by the topsheet 13 and/or backsheet 14 extending beyond the longitudinal margins of the absorbent pad 10 or formed as separate members attached to the longitudinal margins of the absorbent pad. The side tabs 11 are used to prevent leakage of menstrual liquid from contacting wearer's underwear and to secure the absorbent pad 10 to wearer's underwear and maintain the absorbent pad in the wearing position.

The adhesive elements 15 are positioned on the backsheet 14 of the absorbent pad 10. The adhesive elements 15 may be a pressure sensitive adhesive which is formed by conventional technology such as printing, coating or the like. Although the adhesive elements 15 on the backsheet are preferably formed in strips, they can have any shape suitable for maintaining the position of the absorbent pad 10. The adhesive elements 15 on the backsheet 14 are attached to the underwear at the crotch portion when the absorbent pad 10 is installed in the wearer's underwear. The adhesive element 16 is also formed on the back surface of each side tab 11 adjacent the backsheet 14 of the absorbent pad 10. The adhesive elements 16 on the side tabs 11 may be formed from the same material that is used for the adhesive elements 15 on the backsheet 14. The adhesive elements 16 on the side tabs 11 are attached to the outer surface of the wearer's underwear at the crotch portion when the absorbent pad is worn. The adhesive elements 16 of the tabs 11 may be rectangular or any other suitable shape.

Figure 3:
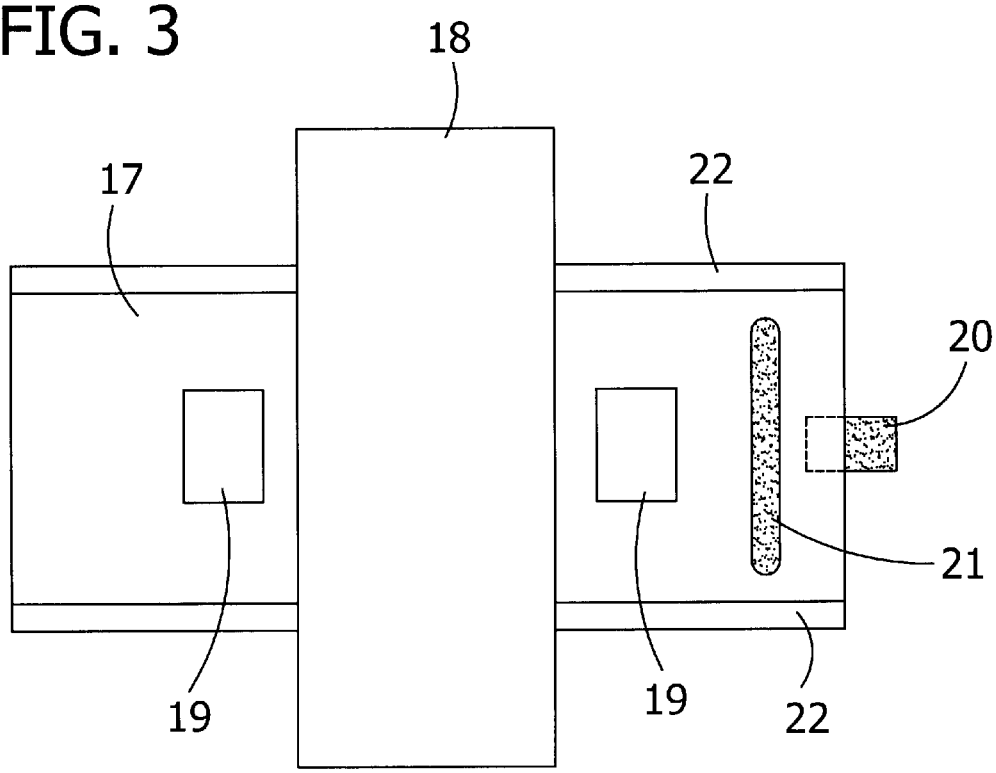
FIG. 3 is a plan view of the inner surface of a wrapper with a central release strip and a pair of tab release members attached thereto.

FIG. 3 illustrates a wrapper 17 which is used to individually package the absorbent pad 10 in FIGS. 1 and 2. The wrapper 17 is made of any appropriate material such as paper, plastic or the like. On the inner surface of the wrapper, a central release strip 18 is permanently affixed so that the longitudinal axes of the release strip 18 and the wrapper 17 are generally perpendicular. The release strip 18 extends beyond the longitudinal edges of the wrapper 17 and is permanently affixed to the inner surface of the wrapper at least at the center portion thereof. On each side of the central release strip 18, a pair of release members 19 are permanently attached to the inner surface of the wrapper. The release members 19 are located at the positions where the adhesive elements 16 of the side tabs 11 are positioned when the adhesive elements 15 on the backsheet 14 are attached to the central release strip 18. The central release strip 18 and the tab release members 19 are permanently attached to the wrapper 17 by conventional technical means such as heat bonding, gluing or the like. An adhesive member 20 is provided at one end of the wrapper. The adhesive member 20 is used to close the package and may be pulled away from the wrapper when unfolding the package. A lateral adhesive strip 21 may also be provided on the inner surface at one end of the wrapper to improve the sealing of the package when closed.

Figure 4:
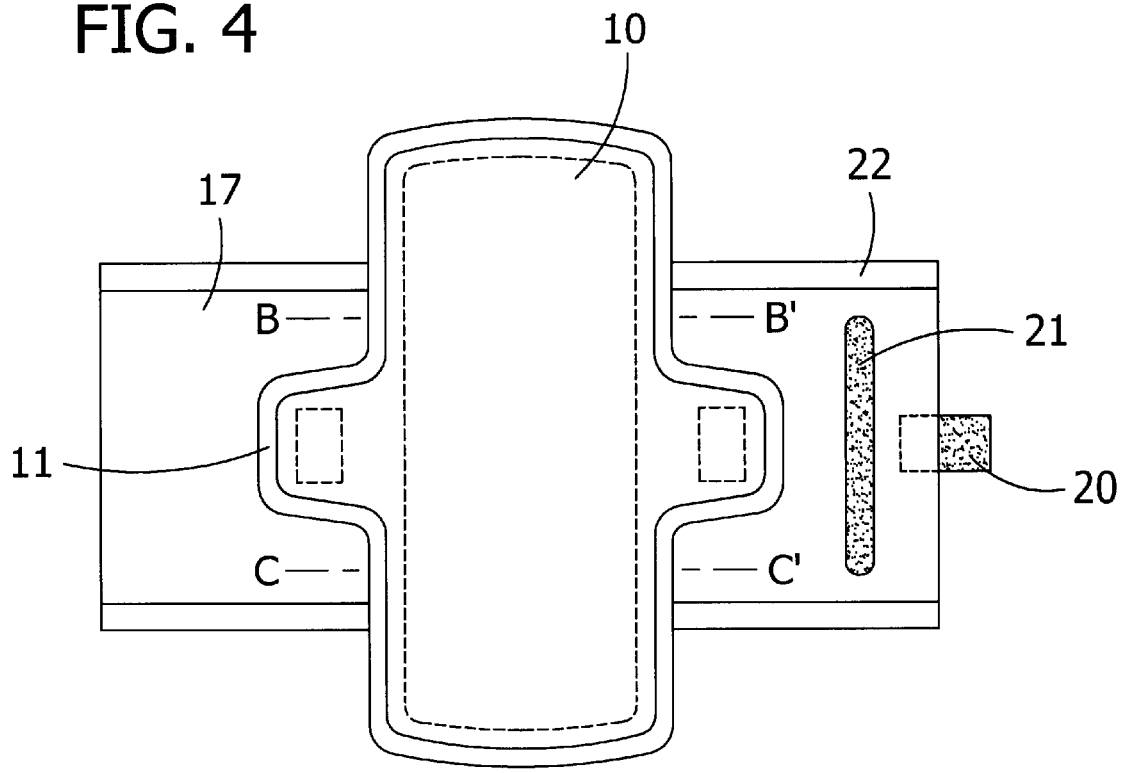
FIG. 4 is a plan view of an absorbent pad attached to the inner surface of the wrapper

According to the invention depicted in FIG. 4, the adhesive elements 15 on the backsheet 14 are releasably attached to the central release strip 18 such that the longitudinal axis of the absorbent pad 10 is generally perpendicular to the longitudinal axis of the wrapper 17. The adhesive elements 16 on the tabs 11 are also releasably attached to the tab release members 19. The central release strip 18 and the tab release members 19 are made of any material suitable for releasably attaching the adhesive elements such as silicone-coated paper or the like. The central release strip 18 and the tab release members 19 protect the surfaces of the adhesive elements 15, 16 on the backsheet 14 and tabs 11, respectively, while the absorbent pad 10 is packaged in the wrapper 17. They also allow the user to detach the absorbent pad 10 from the wrapper 17 after the wrapper is unfolded for use.

Figure 5:
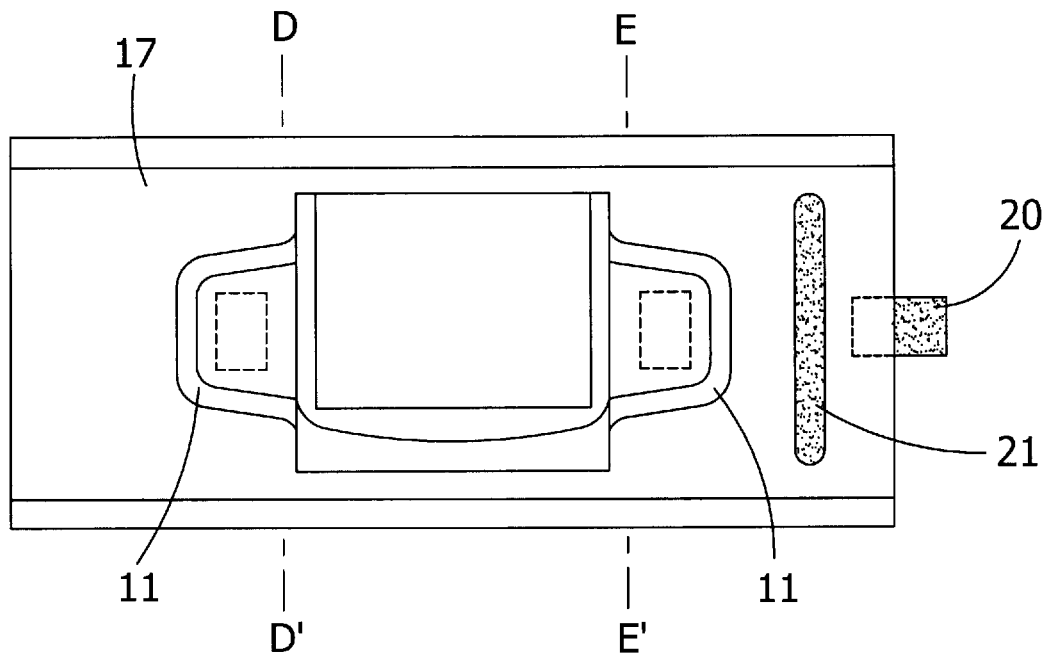
FIG. 5 is a plan view of an absorbent pad attached to the inner surface of the wrapper folded about two spaced-apart lateral fold lines.
Figure 6:
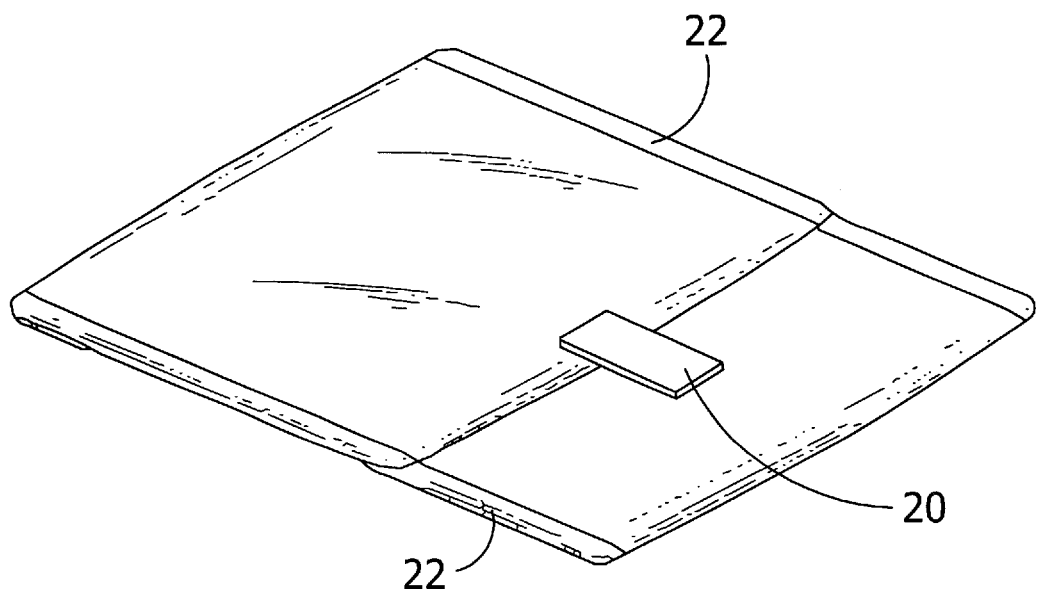
FIG. 6 is a perspective view of an individually packaged absorbent article with a tri-folded wrapper.

FIGS. 5 and 6 show how the absorbent pad 10 is individually packaged according to the present invention. After attaching the absorbent pad 10 to the wrapper 17 as explained with reference to FIG. 4, the absorbent pad is folded about two spaced-apart lateral fold lines or axes B–B', C–C' as depicted in FIG. 4. Preferably, the distance between the lateral fold lines B–B', C–C' is greater than the longitudinal width of the side tabs and smaller than the lateral width of the wrapper 17. When the absorbent pad 10 is folded about the two spaced-apart fold lines, the end portions of the absorbent pad are placed on the topsheet 13 and the end portions may or may not overlap each other depending on the distance between the lateral fold lines. After the absorbent pad 10 is folded about the two lateral fold lines B–B', C–C', the wrapper 17 and tabs 11 are folded as a unit about two spaced-apart lateral fold lines D–D', E–E' as depicted in FIG. 5. Preferably, the lateral fold lines D–D', E–E' are parallel to the longitudinal margins of the tri-folded absorbent pad. When the wrapper is folded about the two lateral fold lines D–D', E"E', the side tabs 11 attached to the release members 19 on the wrapper 17 are also folded about the lateral fold lines D–D', E–E'. When the wrapper 17 is folded about the lateral fold lines D–D', E–E', the side tabs 11 face the backsheet 14 of the folded absorbent pad 10.

After the wrapper 17 is folded, the adhesive member 20 provided at one end of the wrapper is releasably attached to the outer surface of the wrapper to maintain the wrapper in a closed position as depicted in FIG. 6. A landing zone (not shown) may be provided at the location on the outer surface of the wrapper 17 where the adhesive member 20 is attached. As explained above, a lateral adhesive strip 21 provided at one end of the wrapper 17 can be releasably attached to the outer surface of the wrapper to provide a more reliable seal for the package of the absorbent pad. The side margins 22 of the folded wrapper 17 are frangibly sealed by means of conventional technology such as heat bonding, gluing, ultrasonic bonding or the like. Thus, an individually packaged absorbent pad illustrated in FIG. 6 is provided.

Figure 7:
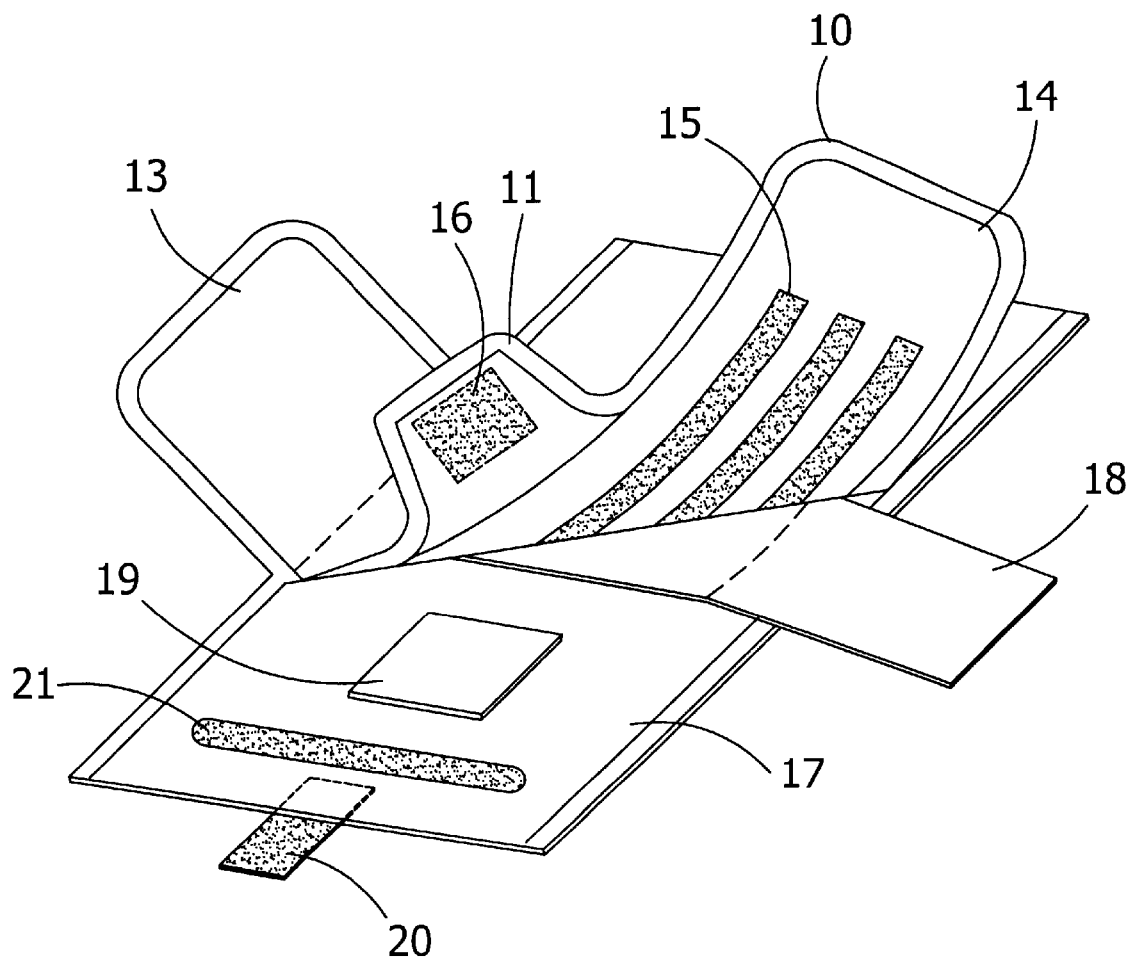
FIG. 7 is a perspective view showing how the absorbent pad is removed from the wrapper according to a first embodiment of the invention.

FIG. 7 illustrates how the absorbent pad 10 is removed from the package for use. In order to open the package for use, the user unfolds the wrapper by pulling the adhesive tape 20 from the outer surface of the wrapper 17. After unfolding the wrapper 17, the user holds an end of the wrapper 17 with one hand and pulls one of the side tabs 11 attached to the respective tab release member 19 with the other hand. As the side tab 11 is pulled out from the wrapper 17, the adhesive element 16 on the side tab is detached from the tab release member 19 and then the adhesive elements 15 on the backsheet 14 of the absorbent pad are detached from the central release strip 18. Finally, the other side tab 11 is detached from the tab release member 19 on the other side of the wrapper 17. Meanwhile, the central release strip 18 and the pair of tab release members 19 remain attached to the wrapper 17 since they are permanently attached to the wrapper. As such, the absorbent pad can be easily removed from the wrapper in a ready-to-use state. The same result can be obtained when the user holds one end of the absorbent pad 10 and pulls the pad out from the central release strip 18.

Prior art absorbent articles use separate release strips and/or sheets to maintain the side tabs in a topsheet facing relationship. In order to secure the absorbent article onto underwear, the user was required to perform an extra step to remove the release strips and/or sheets and unfold the side tabs. According to the present invention, however, the user can remove the absorbent pad from the wrapper in a ready-to-use state without performing this extra step. Further, since the release strip and members are permanently affixed to the wrapper, the user does not have to bother to dispose of the detached release strip and members. Also, in a conventional package of an absorbent pad, the wrapper had to have an area substantially larger than the total area of the unfolded absorbent pad. In this invention, a smaller wrapper can be used because the wrapper is contemplated to wrap around the tri-folded absorbent pad. Accordingly, the present invention has the added economic and environmental advantages of reducing the amount of material required for the wrapper structure.

Figure 8:
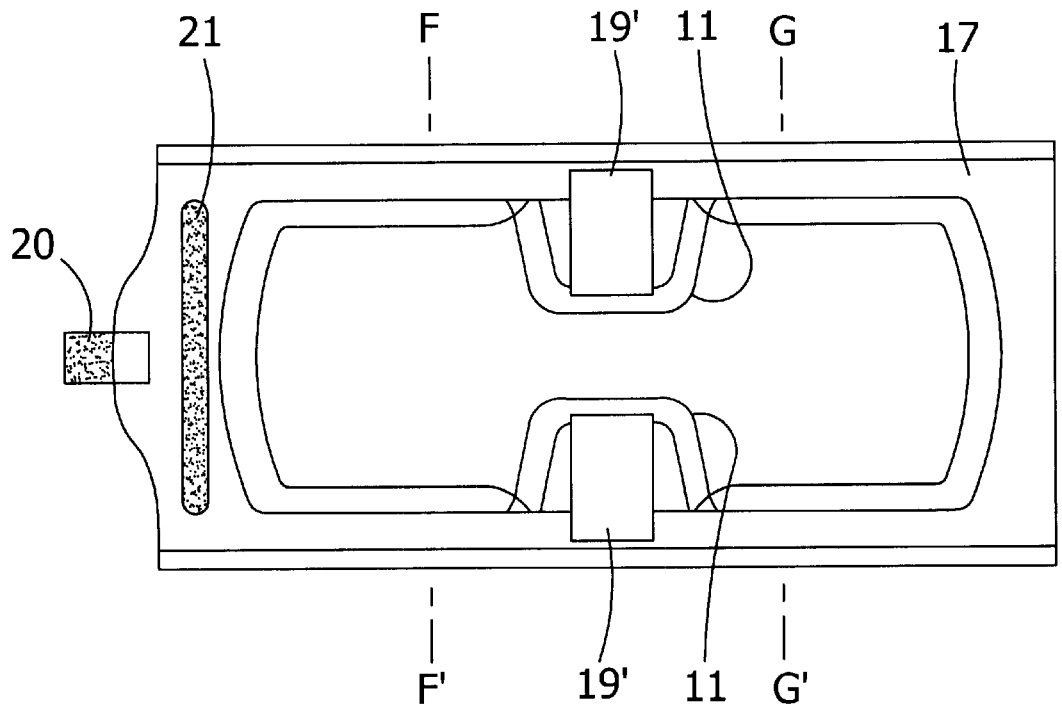
FIG. 8 is a plan view of an absorbent pad attached to the inner surface of the wrapper according to a second embodiment of the invention.
Figure 9:
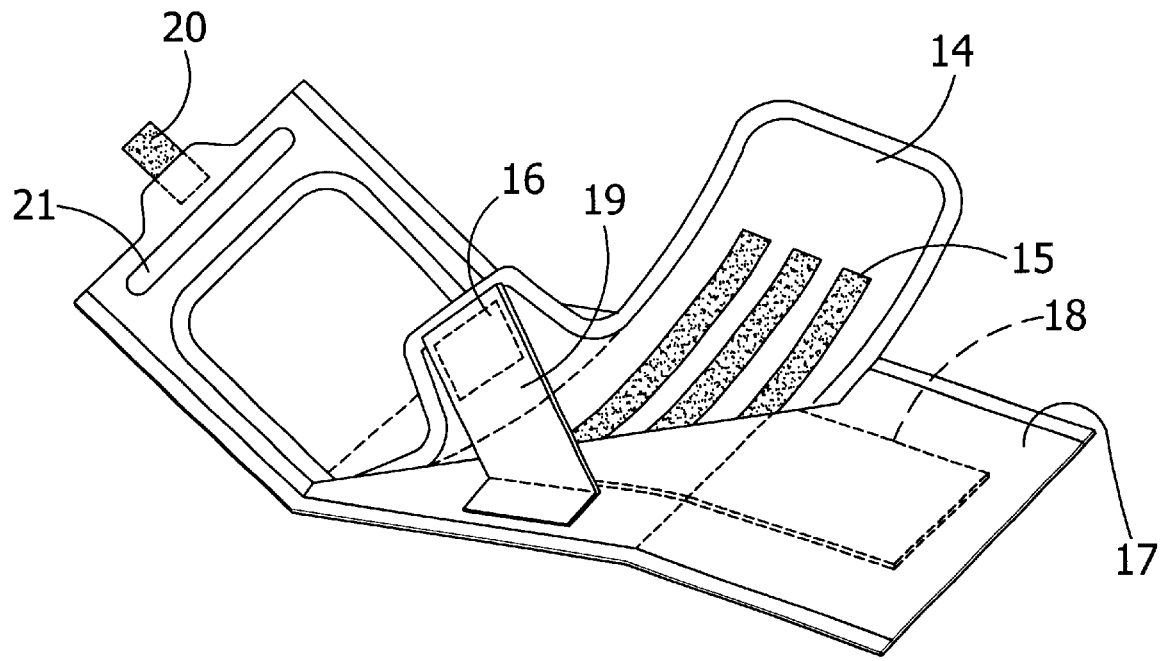
FIG. 9 is a perspective view of an absorbent pad showing how the absorbent pad is removed from the wrapper according to the second embodiment of the invention.

FIGS. 8 and 9 illustrate a second embodiment of the invention where an absorbent pad 10, the same as the absorbent pad depicted in FIG. 1 is attached to a wrapper 17 having a central release strip 18. The central release strip 18 is permanently affixed to the inner surface of a wrapper 17 so that the longitudinal axis of the central release strip 18 is parallel to the longitudinal axis of the wrapper 17. The adhesive elements 15 on the backsheet 14 of the absorbent pad are releasably attached to the central release strip 18 so that the longitudinal axis of the absorbent pad is generally parallel to the longitudinal axes of the wrapper 17 and the central release strip 18. Then, the side tabs 11 are folded over the topsheet 13 and a release member 19' is attached to the adhesive element 16 of each side tab to protect the surface of the adhesive element 16. One end of each tab release member 19' extends beyond the side edge of the absorbent pad and is permanently affixed to the inner surface of the wrapper 17 at a location adjoining the fold line of each side tabs 11.

The wrapper 17 and the absorbent pad 10 are folded as a unit about two spaced-apart laterally oriented fold lines F–F', G–G' and the adhesive member 20 on one end of the wrapper 17 is affixed to the outer surface of the wrapper to complete an individual package of the absorbent pad. As explained with respect to the former embodiment, a landing zone may be provided at the region of the outer surface of the wrapper 17 where the adhesive member 20 is attached. A lateral adhesive strip 21 may be provided at one end of the wrapper to improve the security of the package.

FIG. 9 illustrates how the absorbent pad of FIG. 8 is removed from the wrapper for use. First, the wrapper 17 is unfolded by detaching the adhesive member 20 and the lateral adhesive strip 21 from the outer surface of the wrapper or from the landing zone provided thereon. After the wrapper is unfolded, the absorbent pad 10 is separated from the wrapper 17 by pulling one end of the absorbent pad with one hand, while the other hand holds the wrapper. By doing so, the adhesive elements 15 on the backsheet and the adhesive elements 16 on the side tabs 11 are detached from the central release strip 18 and the tab release members 19', respectively.

Figure 10:
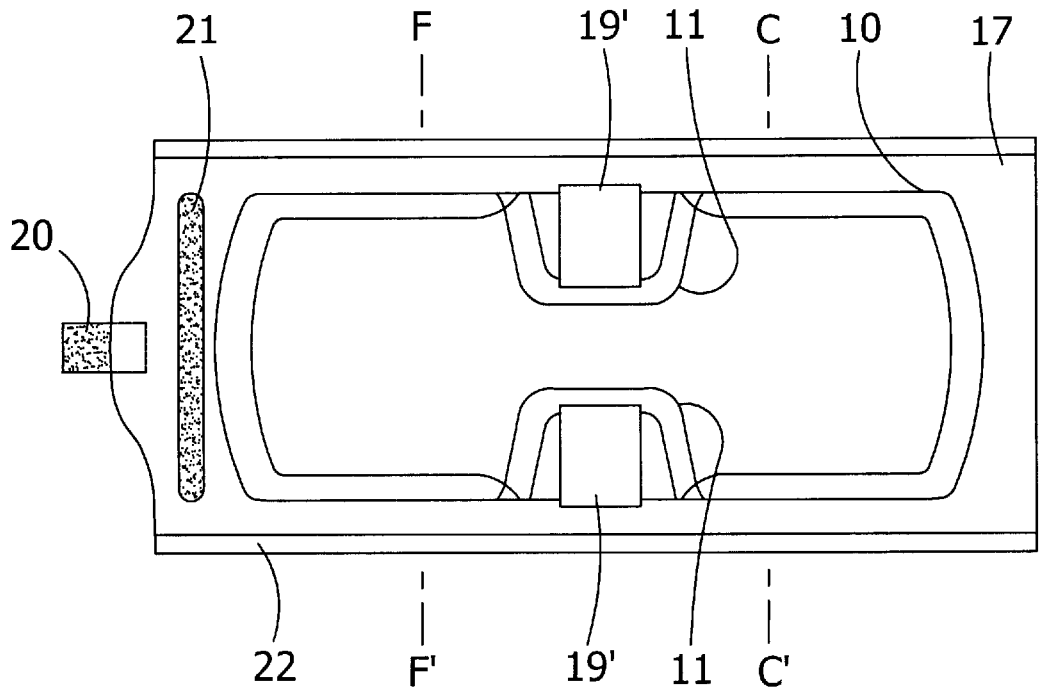
FIG. 10 is a plan view of an absorbent pad attached to the inner surface of the wrapper according to a third embodiment of the invention.
Figure 11:
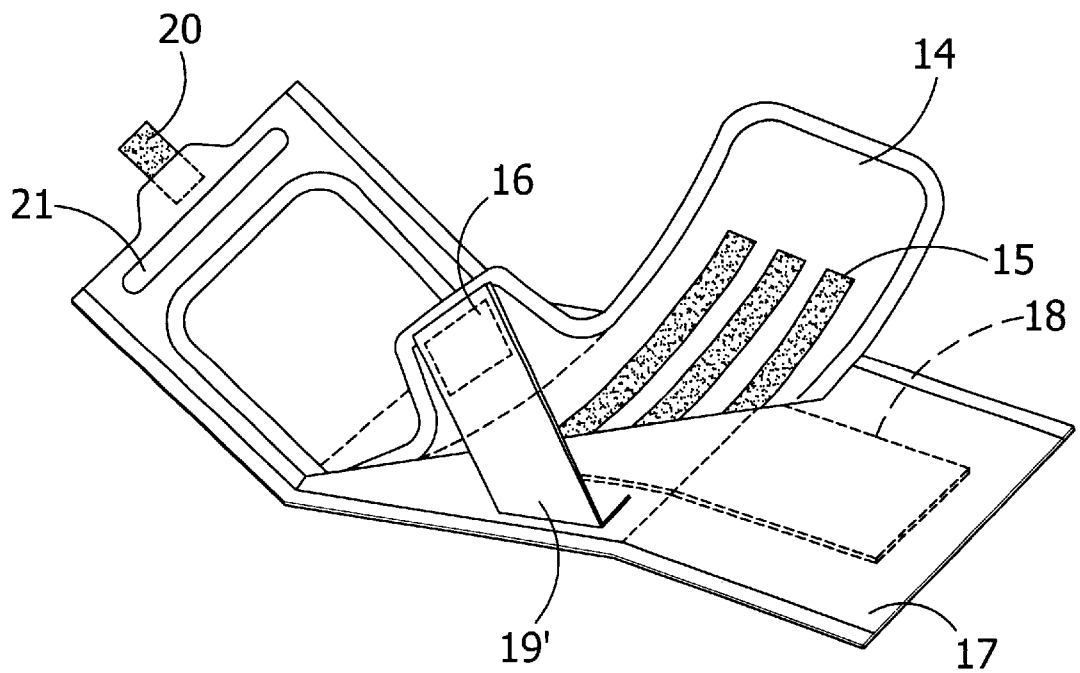
FIG. 11 is a perspective view of an absorbent pad showing how the absorbent pad is removed from the wrapper according to the third embodiment of the invention.

FIGS. 10 and 11 illustrate a third embodiment. Referring to FIG. 10, an absorbent pad 10 is placed on a wrapper 17 in a similar manner as depicted in FIG. 8 except that each of the tab release members 19' extends laterally around the side margin of the absorbent pad 10. The end of the tab release member 19', which extends around a side margin of the absorbent pad, is permanently affixed to the wrapper 17 or the central release strip 18 which is in turn permanently affixed to the wrapper. The absorbent pad 10 in FIG. 10 is packaged as explained with respect to FIGS. 8 and 9. As illustrated in FIG. 11, the individually packaged absorbent article can be unfolded and removed from the wrapper in the same manner as described above with respect to FIG. 9.

The individual package of an absorbent pad and the method for packaging the same explained above with respect to the second and third embodiments effectively protect the topsheet of the absorbent pad and the adhesive elements of the side tabs and the backsheet until the package is unfolded and the absorbent pad is removed from the wrapper. According to the present invention, the absorbent pad can be easily removed from the wrapper in a ready-to-use state, saving the user the step of removing the release strip/members and unfolding the side tabs or the like. In addition, the present invention facilitates the disposal of the removed wrapper and release strip/members, since they remain as a unitary assembly after the absorbent pad is removed for use.

While particular embodiments of the present invention have been illustrated and described, it would be obvious to those skilled in the art that various other changes and modifications can be made without departing from the spirit and scope of the invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An individually packaged absorbent article comprising:
   an absorbent pad having two longitudinal and two lateral margins, said absorbent pad comprising,
      a liquid pervious topsheet,
      a liquid impervious backsheet having adhesive elements formed thereon,
      an absorbent core interposed between said topsheet and said backsheet,
      two tabs each extending outwardly from each longitudinal margin of said absorbent pad and having adhesive elements on the surface coextensive of said backsheet; and
   a wrapper having a central release strip which is attached to said wrapper such that the longitudinal axis of said central release strip generally makes a right angle with respect to the longitudinal axis of said wrapper and a pair of tab release members which are attached to said wrapper on each side of said central release strip,
   wherein, said adhesive elements on said backsheet and said tabs are releasably attached to said central release strip and said tab release members, respectively, and said absorbent pad is folded about at least two spaced-apart lateral fold axes, and said wrapper and said tabs are folded as a unit about at least two spaced-apart lateral fold axes to enclose said folded absorbent pad.

2. The individually packaged absorbent article of claim 1 wherein said central release strip and said tab release members are permanently affixed to said wrapper.

3. The individually packaged absorbent article of claim 1 wherein said wrapper has an adhesive member at one end.

4. The individually packaged absorbent article of claim 2 wherein said wrapper further has a lateral adhesive strip at one end.

5. The individually packaged absorbent article of claim 1 wherein the longitudinal side margins of said wrapper are frangibly sealed.

6. The individually packaged absorbent article of claim 1 wherein the fold axes of said wrapper are aligned with the longitudinal margins of said absorbent pad.

7. The individually packaged absorbent article of claim 1 wherein the longitudinal axis of said central release strip is generally perpendicular to the longitudinal axis of said wrapper.

8. The individually packaged absorbent article of claim 7 wherein the wrapper and the tabs are folded as a unit about said fold lines to enclose said folded absorbent pad.

9. The individually packaged absorbent article of claim 1 wherein the longitudinal axis of said central release strip is generally parallel to the longitudinal axis of said wrapper.

10. The individually packaged absorbent article of claim 9 wherein said tabs are folded over the topsheet, and each of said tab release members is attached to said adhesive element of said tab at one end and attached to said wrapper at the other end.

11. The individually packaged absorbent article of claim 10 wherein said wrapper and said absorbent pad are folded as a unit about said fold lines.

12. A method for individually packaging an absorbent pad having two longitudinal and two lateral margins, a liquid pervious topsheet, a liquid impervious backsheet having adhesive elements formed thereon, an absorbent core interposed between said topsheet and said backsheet, and two tabs each extending outwardly from longitudinal margins of said absorbent pad and having adhesive elements on the surface coextensive of said backsheet, said method comprising the steps of:

provided a wrapper in a generally flat position, affixing a central release strip to said wrapper such that its longitudinal axis generally makes a right angle with respect to the longitudinal axis of said wrapper and affixing a pair of tab release members to said wrapper on each side of said central release strip, releasably attaching said adhesive elements on said backsheet to said central release strip and releasably attaching said adhesive elements on said tabs to said tab release members, folding said absorbent pad about at least two space-apart lateral fold axes, and folding said wrapper and said tabs as a unit about at least two spaced-apart lateral fold axes to enclose said folded absorbent pad.

13. The method according to claim 12 characterized in that said central release strip and said pair of release members are permanently affixed to said wrapper.

14. The method according to claim 12 further comprising a step of frangibly sealing said longitudinal margins of said folded wrapper.

* * * * *

UNITED STATES PATENT AND TRADEMARK OFFICE
CERTIFICATE OF CORRECTION

PATENT NO.   : 6,502,695 B1  
DATED        : January 7, 2003  
INVENTOR(S)  : Doo-Hong Kim et al.

Page 1 of 1

It is certified that error appears in the above-identified patent and that said Letters Patent is hereby corrected as shown below:

Column 6,
Lines 39-40, "having adhesive elements" should read -- having an adhesive element --.
Lines 45-46, "elements on the surface coextensive of said backsheet; and" should read -- elements thereon; and --.
Lines 47-51, "strip which is attached to said wrapper such that the longitudinal axis of said central release strip generally makes a right angle with respect to the longitudinal axis of said wrapper and a pair of tab release members which are attached" should read -- strip attached to said wrapper and a pair of tab release members attached --.
Lines 55-59, "respectively, and said absorbent pad is folded about at least two spaced-apart lateral fold axes, and said wrapper and said tabs are folded as a unit about at least two spaced-apart lateral fold axes to enclose said folded absorbent pad." should read -- respectively, said absorbent pad is folded about at least two spaced-apart fold lines, and said wrapper is folded about at least two spaced-apart fold lines. --.

Column 7,
Line 5, "fold axes of" should read -- fold lines of --.

Column 8,
Lines 2-3, "elements on the surface coextensive of said backsheet, said" should read -- elements thereon, said --.
Lines 7-9, "wrapper such that its longitudinal axis generally makes a right angle with respect to the longitudinal axis of said wrapper and" should read -- wrapper and --.
Lines 16-17, "two space☐apart lateral fold axes, and" should read -- two spaced-apart fold lines, and --.
Lines 19-20, "wrapper and said tabs as a unit about at least two spaced-apart lateral fold axes to" should read -- wrapper about at least two spaced-apart fold lines to --.

Signed and Sealed this

Twenty-third Day of March, 2004

JON W. DUDAS  
*Acting Director of the United States Patent and Trademark Office*